(12) United States Patent
Tuttle et al.

(10) Patent No.: US 7,833,015 B2
(45) Date of Patent: Nov. 16, 2010

(54) KITS AND METHODS FOR CHAIR-SIDE COATING OF ENDODONTIC CONES

(75) Inventors: Richard Tuttle, Layton, UT (US); Jeff Wagner, Sandy, UT (US); Neil Jessop, Sandy, UT (US); Jaleena Fischer-Jessop, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 75 days.

(21) Appl. No.: 11/691,052

(22) Filed: Mar. 26, 2007

(65) Prior Publication Data
US 2008/0241799 A1 Oct. 2, 2008

(51) Int. Cl.
*A61C 5/04* (2006.01)
*A61C 5/02* (2006.01)

(52) U.S. Cl. .................................. 433/224; 433/228.1

(58) Field of Classification Search .................. 433/80, 433/81, 89, 90, 224, 226, 228.1; 523/115, 523/118
See application file for complete search history.

(56) References Cited

U.S. PATENT DOCUMENTS

| | | | |
|---|---|---|---|
| 3,899,830 A | 8/1975 | Malmin | 433/224 |
| 4,256,457 A | 3/1981 | Behring | 433/77 |
| 4,425,094 A | 1/1984 | Tateosian et al. | 433/228.1 |
| 5,275,562 A | 1/1994 | McSpadden | 433/224 |
| 5,328,367 A * | 7/1994 | Johnson | 433/81 |
| 5,425,641 A * | 6/1995 | Fischer | 433/226 |
| 5,860,806 A | 1/1999 | Pranitis, Jr. et al. | 433/80 |
| 6,025,406 A | 2/2000 | Oxman et al. | 522/14 |
| 6,082,999 A | 7/2000 | Tcherny et al. | 433/80 |
| 6,500,004 B2 | 12/2002 | Jensen et al. | 433/228.1 |
| 6,729,879 B2 * | 5/2004 | Allred et al. | 433/226 |
| 6,805,842 B1 * | 10/2004 | Bodner et al. | 422/102 |
| 6,957,958 B2 | 10/2005 | Rowe et al. | 433/89 |
| 6,986,662 B2 | 1/2006 | Haschke | 433/228.1 |
| 2003/0199605 A1 * | 10/2003 | Fischer | 523/116 |
| 2004/0137404 A1 | 7/2004 | Koch et al. | 433/81 |
| 2004/0202986 A1 | 10/2004 | Haschke | |
| 2005/0048435 A1 | 3/2005 | Badoz | 433/32 |
| 2005/0066854 A1 | 3/2005 | Jia | 106/35 |
| 2005/0123878 A1 * | 6/2005 | Lee | 433/80 |
| 2005/0136382 A1 | 6/2005 | Haschke | 433/224 |
| 2007/0065781 A1 * | 3/2007 | Wagner et al. | 433/224 |
| 2007/0077538 A1 | 4/2007 | Musikant et al. | |
| 2007/0184413 A1 * | 8/2007 | Musikant et al. | 433/224 |

* cited by examiner

OTHER PUBLICATIONS

Office Action dated Dec. 11, 2009 cited in U.S. Appl. No. 12/184,549.
Office Action dated Jun. 11, 2010 cited in U.S. Appl. No. 12/184,549.

*Primary Examiner*—Ralph A Lewis
*Assistant Examiner*—Michael R Ballinger
(74) *Attorney, Agent, or Firm*—Workman Nydegger

(57) ABSTRACT

Kits and methods facilitate chair-side coating of an endodontic cone for improved sealing between the hydrophilic root canal tissue, the hydrophobic elastomer substrate of the endodontic cone, and a hydrophilic sealing resin. The kit includes one or more endodontic cones (e.g., formed of gutta percha) and a micro-dose container containing an adhesive composition. The practitioner can dip the cones into the adhesive composition so as to coat the cones chair-side, just prior to use. The adhesive composition includes an adhesive resin compound comprising at least one hydrophobic region and at least one hydrophilic region. The hydrophobic region is compatible with the hydrophobic elastomer substrate of the endodontic cone, while the hydrophilic region is compatible with a hydrophilic endodontic sealing resin.

23 Claims, 5 Drawing Sheets

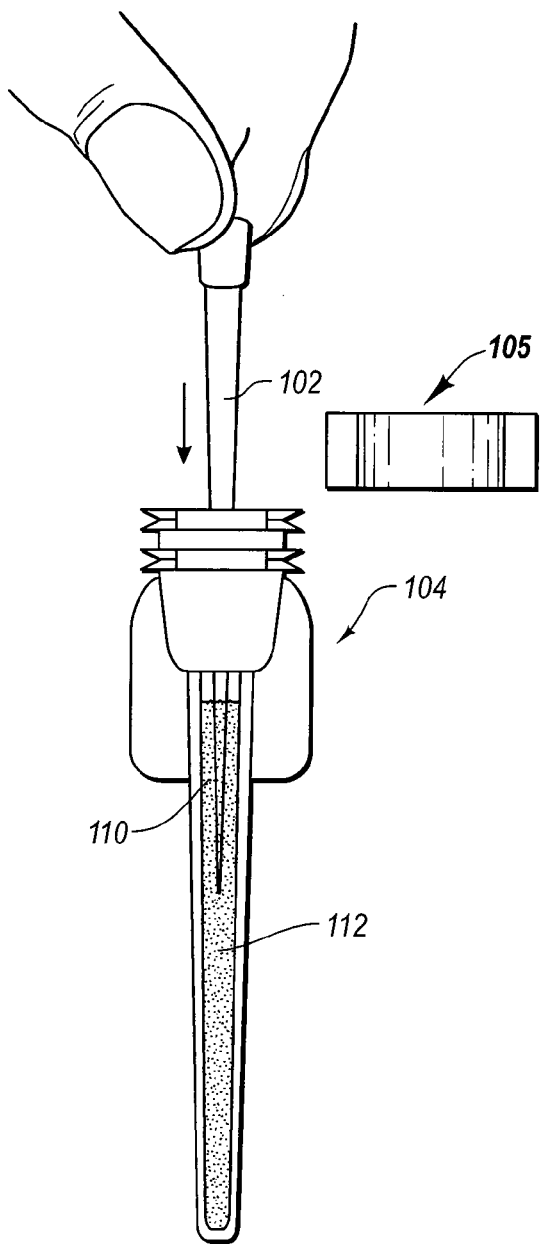
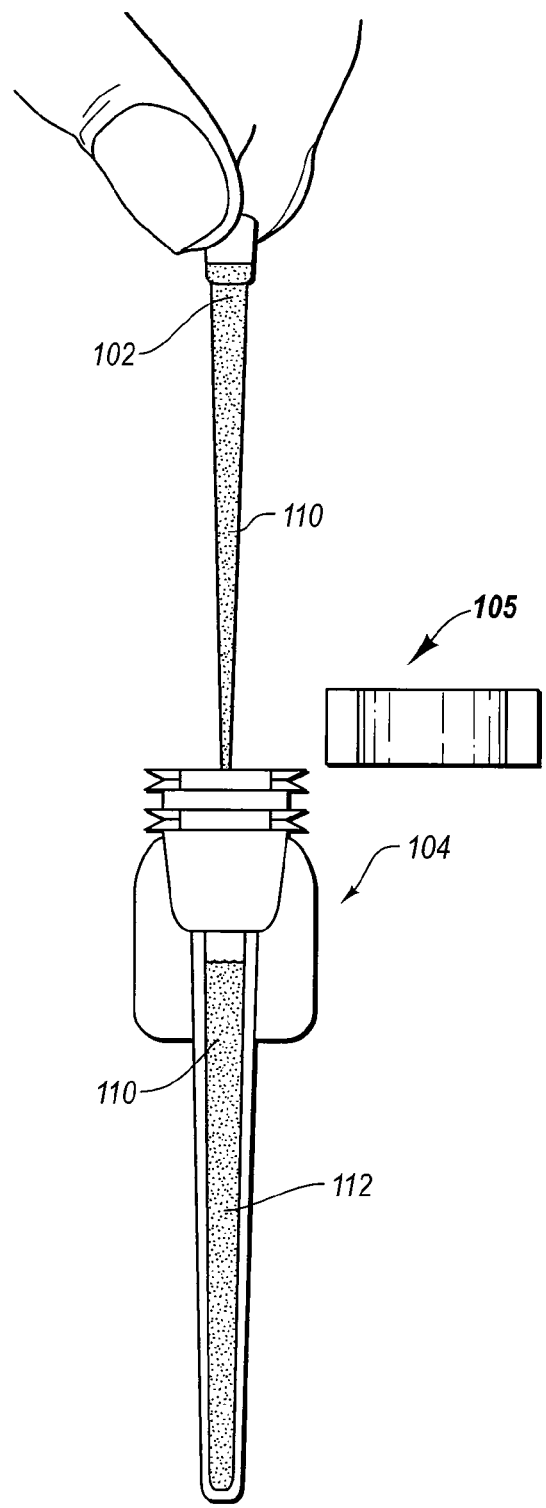
Fig. 4A
Fig. 4B

KITS AND METHODS FOR CHAIR-SIDE COATING OF ENDODONTIC CONES

BACKGROUND OF THE INVENTION

1. The Field of the Invention

The present invention relates to the field of dentistry, more particularly to endodontic cones, such as those made of gutta percha, used in filling root canal chambers.

2. The Relevant Technology

When a dental practitioner performs a root canal, pulp and other material in the root canal chamber is removed. Once a dentist has removed diseased and soft tissue from a tooth's root canal, the chamber must be filled. The purpose of filling the root canal is to seal the area, and to eliminate the possibility of bacterial attraction and infection in the chamber. Filling and sealing the chamber is necessary to prohibit material from draining into the canal, which could attract bacterial contamination of the root canal chamber. In addition, filling the chamber provides a base that may be drilled out later for placement of one or more posts to which may be mounted a crown or other restorative appliance.

The current method of filling the root canal is by inserting shaped cones of gutta percha into the prepared root canal. Gutta percha typically includes a matrix of trans-isoprene, zinc oxide filler, a radiopacifier such as bismuth, barium or strontium, wax or resin, color pigment, plasticizers and other additives. One difficulty with using gutta percha has been that it does not readily bond to and seal against the tooth tissue. Tooth tissue is quite hydrophilic, while gutta percha itself is extremely hydrophobic. Typical endodontic pastes, used to bond and seal the gutta percha to the tooth tissue, comprise zinc oxide and eugenol. This mixture is also hydrophobic, and while it bonds quite well to the gutta percha, its bond with hydrophilic tooth tissue is often poor. In addition, eugenol is believed to act as a polymerization inhibitor, which can also result in poor bonding and sealing in the event polymericable resins are used.

Recently, hydrophilic resins have been developed which bond much better to tooth tissue, but they may still bond poorly to gutta percha because of its extremely hydrophobic nature. The result may be a root canal chamber that is not completely sealed, which increases the chance of irritation of the affected area or bacterial contamination, leading to infection and possible failure of the root canal. The level of discomfort and pain associated with an irritated, inflamed, and/or infected root canal area can be great, followed by loss of the tooth.

As one solution to this problem, U.S. Pat. No. 6,986,662 proposes providing an endodontic cone to which a particular adhesive coating has been attached during manufacture so as to render the cone more chemically compatible with a hydrophilic sealing resin. The adhesive includes a hydrophobic portion that is chemically compatible with the gutta percha substrate and a hydrophilic portion that is chemically compatible with a hydrophilic resin. The adhesive may be applied by dipping or brushing during manufacture. While such a manufactured endodontic cone appears to solve the problem of poor bonding between the tooth tissue, the sealing resin, and the gutta percha, the present inventors have found the manufacturing process including coating of the adhesive to be extremely messy and difficult to perform. For example, the adhesive can easily clog and gum up manufacturing equipment, requiring frequent shut downs, cleaning, and maintenance, which makes it difficult and relatively expensive to produce coated endodontic cones on a mass economic scale.

It would be an improvement in the art to provide kits and methods that would solve the poor bonding issues, while also minimizing or eliminating the difficulties and messiness associated with current manufacturing methods.

BRIEF SUMMARY OF THE PREFERRED EMBODIMENTS

The present invention provides kits and methods that advantageously allow a practitioner to apply an adhesive coating to an endodontic cone chair-side just prior to inserting the coated cone into the root canal. The kit includes one or more endodontic cones formed of a hydrophobic elastomer substrate (e.g., gutta percha), each cone being sized and shaped so as to be at least partially insertable into an exposed root canal of a tooth. The kit also includes a micro-dose container containing an adhesive composition into which the endodontic cone is inserted so as to coat at least a portion of the cone with the adhesive composition and facilitate successful bonding between the hydrophobic substrate and a hydrophilic sealing resin used within the root canal. The micro-dose container advantageously has a length, diameter, and volume configured to accept the endodontic cone so as to allow the cone to be coated with the adhesive composition. For example, an exemplary micro-dose container may be sized so as to advantageously hold sufficient material to fill a single root canal. Such an exemplary micro-dose container may have a volume between about 20 and about 55 micro-liters, more preferably between about 25 and about 50 micro-liters, and most preferably between about 30 and about 40 micro-liters. The inside diameter of the distal portion of the chamber is preferably between about 0.04 inch and about 0.09 inch, more preferably between about 0.045 inch and about 0.07 inch, and most preferably between about 0.05 inch and about 0.065 inch. Wall thickness of the chamber is typically between about 0.02 inch and about 0.04 inch (e.g., about 0.025 inch). The overall length of the micro-dose container is preferably between about 0.75 inch and about 1.5 inches, more preferably between about 1 inch and about 1.25 inch.

The adhesive composition includes an adhesive resin compound comprising at least one hydrophobic region and at least one hydrophilic region. The hydrophobic region is compatible with the hydrophobic elastomer of the endodontic cone so as to chemically and/or physically adhere to the hydrophobic elastomer. The hydrophilic region is chemically compatible with a hydrophilic endodontic resin. The adhesive facilitates the formation of a good seal between the hydrophilic tooth tissue of the canal chamber and the endodontic cone, while the inventive kit and method facilitate coating of the endodontic cone(s) while overcoming the difficulties associated with coating during mass manufacture.

The endodontic cones may be dipped into the adhesive composition contained within the micro-dose container so as to coat at least a portion of the surface of the endodontic cone substrate. Advantageously, performing the coating chair-side by simply dipping the cone into the composition within the micro-dose container results in little or no mess. In addition no curing or powder coating is required to prevent adhesion between cones during shipment and storage. Because the hydrophobic region is compatible with the hydrophobic material comprising the endodontic cone, the hydrophobic region of the adhesive component will tend to orient itself toward the endodontic cone while the hydrophilic region will tend to orient itself away from the endodontic cone, thereby creating a hydrophilic surface on the endodontic cone.

Advantageously, it will often be unnecessary to cure the adhesive composition prior to insertion of the coated cone into the root canal, as the curable adhesive composition can be cured by components within the sealing composition used to seal around the endodontic cone within the root canal. Although not required, the practitioner may wish to partially or fully cure the adhesive composition and/or apply a powder coating so as to reduce adhesion between multiple coated endodontic cones. For example, this may be helpful if several cones are to be prepared, placed on a tray or other holding device chair-side, and then inserted into the prepared root canal.

In practice, the root canal chamber is prepared by removing diseased and surrounding tissue. The endodontic cone may be coated before or after preparing the root canal chamber. Once both of these steps have been completed, the coated endodontic cone is inserted into the chamber. One or more cones may be used as necessary so as to fill the chamber. An endodontic sealing composition is introduced into the prepared canal, which can then be cured to provide a good seal of the root canal chamber. When using a dipped endodontic cone that has not been cured prior to insertion, the presence of initiators within the sealing composition will advantageously initiate curing of the adhesive component within the adhesive coating, resulting in strong bonds between the hydrophobic elastomer substrate of the endodontic cone, the adhesive composition, the sealing composition, and the hydrophilic tooth tissue. A hydrophilic sealing composition, such as Endo-REZ, available from Ultradent Products, Inc., may be used, and will bond well to the tooth tissue because of its hydrophilic nature and its ability to penetrate into dentinal tubules. Once the root canal chamber has been filled, the hub of the cone may be removed.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIGS. 4A-4B illustrate an endodontic cone being inserted and withdrawn, respectively, from the chamber of the micro-dose container of the kit of FIG. 1;

DETAILED DESCRIPTION OF THE PREFERRED EMBODIMENTS

I. Introduction

The present invention provides kits and methods for chair-side coating of an endodontic cone just prior to placement into a root canal. The kit includes one or more endodontic cones that comprise a hydrophobic elastomer substrate (e.g., gutta percha) that is sized and shaped so as to be at least partially insertable into an exposed root canal of a tooth. The kit also includes a micro-dose container containing an adhesive composition into which the cone is adapted to be inserted so as to coat at least a portion of the cone with the adhesive composition and render the cone more chemically compatible with a hydrophilic endodontic resin. The adhesive composition includes an adhesive resin compound comprising a hydrophobic portion for adhering to the hydrophobic elastomer of the endodontic cone and a hydrophilic portion that is chemically compatible with a hydrophilic sealing resin. The coated endodontic cone facilitates complete sealing between the endodontic cone, an endodontic sealing resin, and the hydrophilic tooth tissue of a root canal chamber. Advantageously, the inventive kit and method allow a practitioner to prepare the coated endodontic cone immediately prior to insertion of the cone within the root canal of the tooth, while minimizing messiness associated with preparing the coated endodontic cone ion a mass scale.

As used herein, the terms "endodontic sealing resin" and "endodontic sealing composition" refer to any endodontic resin or composition used for sealing a root canal chamber. The resin or composition may be hydrophobic or hydrophilic.

As used herein, the term "methacrylate" refers to any methacrylate resin, while the term "acrylate" refers to any acrylate resin. Hydroxyethylmethacrylate (HEMA) is an example of a methacrylate resin.

II. An Exemplary Kit for Chair-Side Coating of an Endodontic Cone

Figure 1:
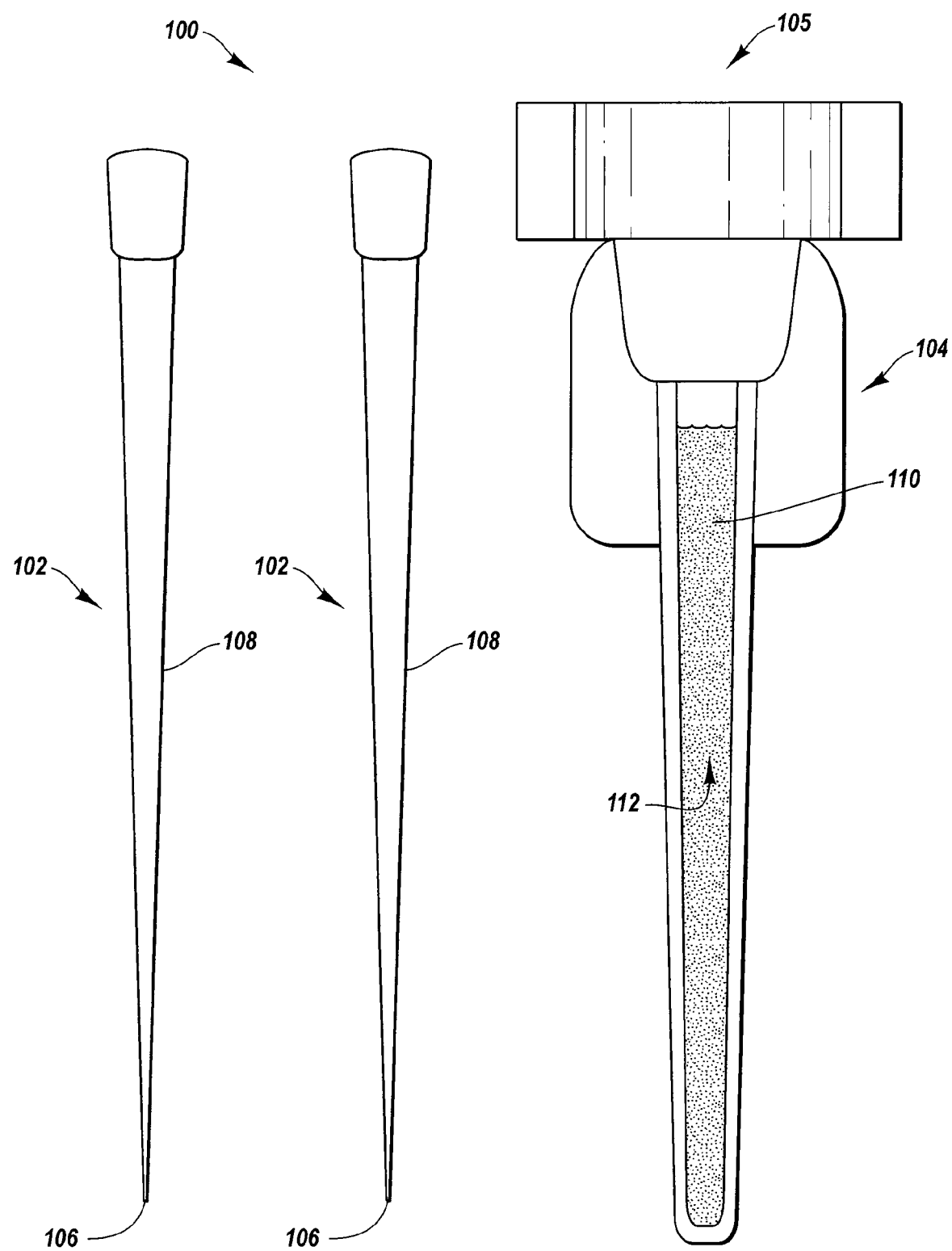
FIG. 1 illustrates an exemplary kit including a plurality of endodontic cones and a microdose container containing an adhesive composition for chair-side coating of the endodontic cones.

FIG. 1 is a perspective view of an exemplary kit 100 according to the present invention including one or more endodontic cones 102 and a micro-dose container 104 including a cap 105. Cap 105 may be threadably coupleable to container 104 so as to allow the practitioner to close the opening of container 104 when not in use. Alternative coupling mechanisms will be apparent to one skilled in the art. The micro-dose container 104 advantageously has a length, diameter and volume configured to accept the endodontic cone so as to allow the cone to be coated with the adhesive composition. For example, an exemplary micro-dose container may be sized so as to advantageously hold sufficient material to fill a single root canal. Such an exemplary micro-dose container may have a volume between about 20 and about 55 micro-liters, more preferably between about 25 and about 50 micro-liters, and most preferably between about 30 and about 40 micro-liters. The inside diameter of the distal portion of the chamber is preferably between about 0.04 inch and about 0.09 inch, more preferably between about 0.045 inch and about 0.07 inch, and most preferably between about 0.05 inch and about 0.065 inch. Wall thickness of the chamber is typically between about 0.02 inch and about 0.04 inch (e.g., about 0.025 inch). The overall length of the micro-dose container is preferably between about 0.75 inch and about 1.5 inches, more preferably between about 1 inch and about 1.25 inch. Such a micro-dose container is easily grasped between a thumb and index finger of a practitioner, allowing the other hand to be used to insert an endodontic cone into the micro-dose container so as to coat the cone while chair-side, immediately prior to use.

Endodontic cones 102 each include an insertion tip 106 and an outer surface 108 to which can be applied an adhesive composition 110 initially stored within a chamber 112 of micro-dose container 104. The endodontic cones 102 are formed of a hydrophobic elastomer substrate that is sized and shaped so as to be at least partially insertable into an exposed root canal of a tooth. Gutta percha is one example of a hydrophobic elastomer substrate used to form the endodontic cones. Other exemplary materials include synthetic rubber, natural rubber, a derivative of natural rubber, silicone rubber, neoprene, isoprene, or polybutadiene.

The adhesive 110 renders the outer surface 108 of cone 102 more chemically compatible with a hydrophilic endodontic resin and facilitates complete sealing between the endodontic cone, an endodontic sealing resin, and the hydrophilic tissue defining the root canal chamber. The adhesive composition 110 includes an adhesive resin compound comprising at least one hydrophobic region that chemically or physically adheres to the hydrophobic elastomer substrate of the endodontic cone 102, and at least one hydrophilic region that is hydrophilic so as to be more chemically compatible with a hydrophilic endodontic resin.

The adhesive composition 110 is advantageously provided within kit 100 so as to allow the practitioner to dip the endodontic cone into the chamber 112 of micro-dose container 104 so as to coat adhesive composition 110 over at least a portion of outer surface 108 of cone 102. Applying the adhesive composition chair-side in this manner is advantageous as there is little or no mess associated with the procedure (as compared to coating the cones during mass production, which has been found to be quite messy), and it is not necessary to cure the adhesive composition after coating and prior to insertion into the Curing may be advantageously accomplished within the root canal, as curing may be accomplished by an initiator-amine activator system already present within the endodontic sealing resin. According to one such embodiment, an initiator (e.g., benzoyl peroxide) or an amine activator (i.e., a tertiary amine such as P-Tide) may be included within the adhesive composition 110. The complementary initiator component may advantageously be included in the sealing resin. Upon contact of the adhesive composition with the sealing resin, curing of the adhesive resin compound is initiated as the two initiator components are brought together. Including either an initiator or an amine activator within the adhesive composition and the complementary component in the sealing resin enables complete curing of the adhesive composition.

In addition to the curable adhesive compound and an initiator or an amine activator, the composition 110 may additionally comprise a thinning agent, which is helpful in reducing the overall viscosity of the adhesive composition where the adhesive resin compound is otherwise relatively viscous. In one embodiment, the thinning agent may comprise one or more polymerizable resin components, e.g., polymerizable acrylate or methacrylate resins, examples of which include, but are not limited to, triethylene dimethacrylate, butyl methacrylate, butyl dimethacrylate, hexanediol dimethacrylate, polyethyleneglycol diacrylate (PEGDA) and isobornyl methacrylate. The thinning agent is advantageously suitable for use within the oral cavity, and acts to reduce the relatively high viscosity of the adhesive resin compound (e.g., a methacrylated polybutadiene).

The adhesive resin compound is preferably included within a range of about 5% to about 50% by weight of the adhesive composition, more preferably in a range of about 10% to about 40% by weight, and most preferably in a range of about 15% to about 30% by weight of the adhesive composition.

The thinning agent is preferably included within a range of about 50% to about 95% by weight of the adhesive composition, more preferably in a range of about 60% to about 85% by weight, and most preferably in a range of about 65% to about 80% by weight of the adhesive composition.

Any initiator or amine activator is preferably included in an amount in a range of about 0.01% to about 5% by weight of the adhesive composition, more preferably in a range of about 0.1% to about 3% by weight, and most preferably in a range of about 0.2% to about 2% by weight of the adhesive composition.

A free-radical scavenging antioxidant inhibitor (e.g., butylated hydroxytoluene-BHT) may also be included so as to prolong the shelf life of the adhesive composition, particularly when the adhesive composition includes an initiator or an amine activator (which form free radicals). The inhibitor acts to remove free radicals that may be formed prematurely (e.g., during storage of the adhesive composition) that if not removed may significantly reduce the shelf life of the adhesive composition. Any inhibitor is preferably included in an amount in a range of about 0.001% to about 1% by weight of the adhesive composition, more preferably in a range of about 0.01% to about 0.5% by weight, and most preferably in a range of about 0.025% to about 0.1% by weight of the adhesive composition.

Figure 2:
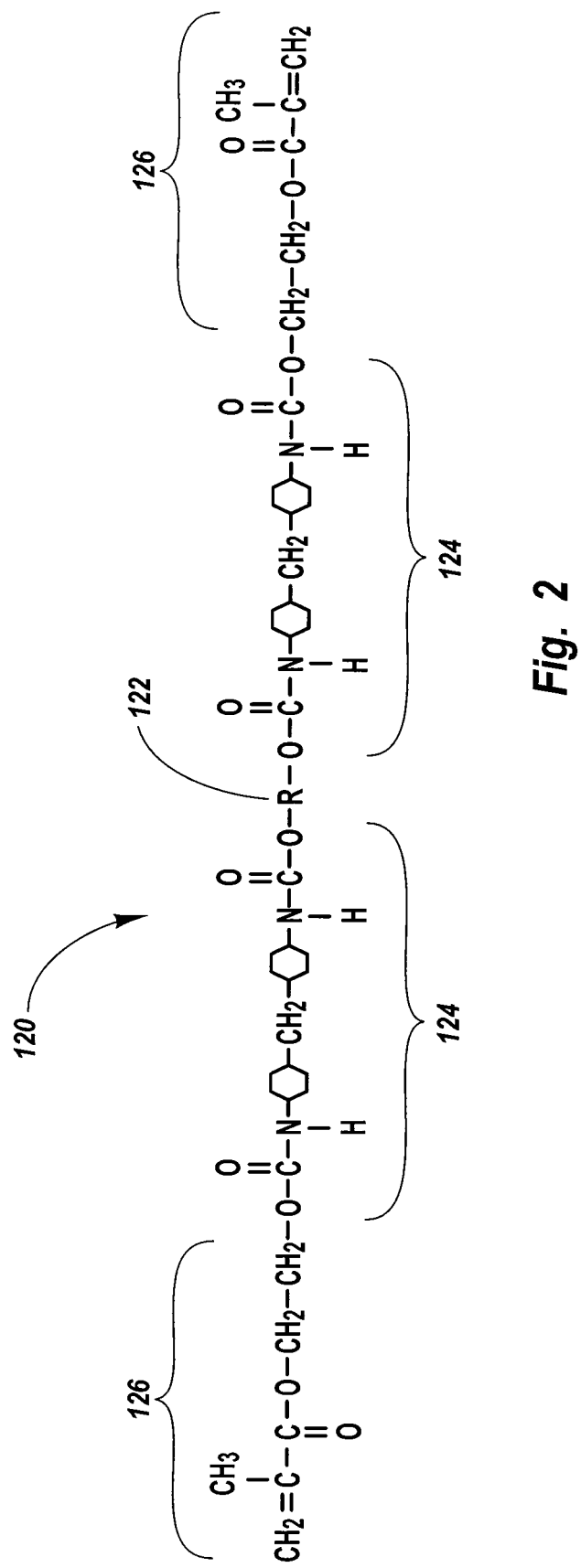
FIG. 2 illustrates the chemical structure of a preferred curable adhesive resin compound included within the adhesive composition of the kit of FIG. 1.

The adhesive resin compound includes a hydrophobic region compatible with the hydrophobic elastomer substrate of the endodontic cone, and also a hydrophilic region that is chemically compatible with a hydrophilic endodontic sealing resin. As illustrated in FIG. 2, one example of a suitable adhesive resin compound 120 contains a hydrophobic backbone "R" designated as 122, a diurethane constituent 124 on either side of the hydrophobic backbone 122, and a methacrylate constituent 126 attached to each free end of the two diurethane constituents 124. In the illustrated embodiment, the configuration of the adhesive composition is: Methacrylate-Urethane-Hydrophobic Backbone-Urethane-Methacrylate. Nevertheless, it will readily be appreciated that some or all of the adhesive resin compound may comprise other configurations, examples of which include: Methacrylate-Urethane-Hydrophobic Backbone and/or Methacrylate-Urethane-Hydrophobic Backbone-Urethane-Hydrophobic Backbone-Urethane-Methacrylate.

The hydrophobic backbone "R" advantageously comprises one or more hydrophobic polymers, oligomers or constituents that are chemically compatible with the hydrophobic elastomer of the endodontic cone. In the case where the elastomer comprising the endodontic cone has unsaturated units (e.g., gutta percha), at least a portion of the hydrophobic polymer, oligomer or constituents comprising the hydrophobic backbone may advantageously contain ethylenically unsaturated units that are, at least in theory, able to cross link with the unsaturated units within the elastomer comprising the endodontic cone.

In one embodiment, at least a portion of the hydrophobic backbone "R" comprises at least one of polybutadiene or a derivative thereof (e.g., substituted polybutadiene). The individual units comprising the polybutadiene polymer may include cis groups, trans groups, or both. In addition, a portion of the units may comprise vinyl substituted ethylene groups (e.g., where one butadiene molecule reacts with the number 2 carbon of another butadiene molecule instead of the number 4 carbon during polymerization). To provide additional functionality, at least some of the C=C double bonds may be epoxidized to form oxirane units (either cis, trans or both, as well as on at least some of the vinyl groups where present). The hydrophobic backbone may advantageously comprise combinations of one or more of the foregoing constituents.

An example of a hydrophobic polymer suitable for use in forming the hydrophobic backbone of an adhesive composition for use within kits and methods according to the invention includes an epoxidized derivative of polybutadiene. One specific example has the following physical properties:

| | |
|---|---|
| Epoxy Value (meq/g) | 2-2.5 |
| Epoxy Equivalent weight | 400-500 |
| Oxirane Oxygen (%) | 3.4 |
| Viscosity (mPas @ 300° C.) | 7000 |
| Water (wt % max) | 0.10 |
| Specific Gravity | 1.01 |
| Hydroxyl Value (meq/g) | 1.70 |

Approximate Microstructure:

| | |
|---|---|
| Epoxy cis (mol %) | 7-10 |
| Epoxy trans (mol %) | 8-12 |
| Vinyl Double Bonds (mol %) | 22 |
| 1,4-Double Bonds (mol %) | 53-60 |
| Opened Epoxy (mol %) | 2.5 |

Another specific example has the following physical properties:

| | |
|---|---|
| Epoxy Value (meq/g) | 3-4 |
| Epoxy Equivalent weight | 260-330 |
| Oxirane Oxygen (%) | 4.8-6.2 |
| Viscosity (mPas @ 300° C.) | 22,000 |
| Water (wt % max) | 0.10 |
| Specific Gravity | 1.01 |
| Hydroxyl Value (meq/g) | 1.70 |

Approximate Microstructure:

| | |
|---|---|
| Epoxy cis (mol %) | 7-10 |
| Epoxy trans (mol %) | 8-12 |
| Vinyl Double Bonds (mol %) | 22 |
| 1,4-Double Bonds (mol %) | 53-60 |
| Opened Epoxy (mol %) | 2.5 |

In general, the backbone preferably has a molecular weight between about 500 and 2000 (number average), more preferably between about 800 and 1600 (number average), and most preferably between about 1000 and 1400 (number average). In one embodiment, at least a portion of the hydrophobic backbone comprises an epoxidized derivative of polybutadiene having a molecular weight of about 1200 (number average). The backbone may additionally or alternatively comprise at least one of polyethylene glycol (PEG), polypropylene glycol (PPG), polyhexatetramethylene-etherglycol (PTMEG) and/or derivates thereof.

As seen in FIG. 2, the exemplary adhesive resin compound 120 is illustrated as also including one or more diurethane constituents 124. The illustrated diurethane constituent has the chemical structure:

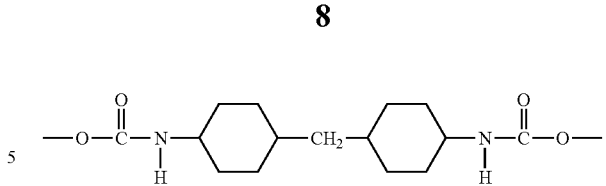

The illustrated diurethane 124 includes cyclohexyl groups separated by a methylene group. Although the illustrated diurethane 124 is currently preferred, any of various urethanes containing NHCOO linkages may be used (e.g., separated by one or more linear alkyl groups and/or one or more aryl groups, such as phenyl).

As seen in FIG. 2, the exemplary adhesive resin compound also contains one or more methacrylate constituents 126. The illustrated methacrylate has the chemical structure:

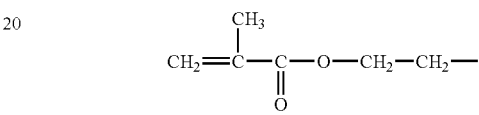

The illustrated methacrylate constituents 126 are each located adjacent to a respective urethane constituent 124 and form the terminal ends of the adhesive resin compound 120. The exemplary methacrylate constituents 126 are derived from HEMA that has been condensed with the diurethane constituent. Methacrylate constituent 126 is an example of a hydrophilic constituent that is compatible with a hydrophilic endodontic sealing resin. Any methacrylate or acrylate constituent may be used in place of illustrated methacrylate constituent 126 in the adhesive resin compound 120.

The adhesive resin compound illustrated in FIG. 2 is one example of an adhesive resin compound 120. Any compound containing at least one hydrophobic region (e.g., a hydrophobic polymer chain) that is able to adhere to the hydrophobic elastomer substrate of outer surface 108, and that also contains at least one hydrophilic region (e.g., a methacrylate or acrylate bonded to the hydrophobic region by means of, e.g., a diurethane constituent) that is chemically compatible with a hydrophilic endodontic sealing resin may alternatively be used. The adhesive resin compound 120 illustrated in FIG. 2 may be manufactured through a multi-step process in which the various portions (e.g., a hydrophobic backbone, one or more diurethane constituents, and one or more methacrylate constituents) are joined together. Exemplary processes are described in U.S. Pat. No. 6,986,662, herein incorporated by reference.

III. Methods for Chair-Side Coating of an Endodontic Cone

Figure 3:
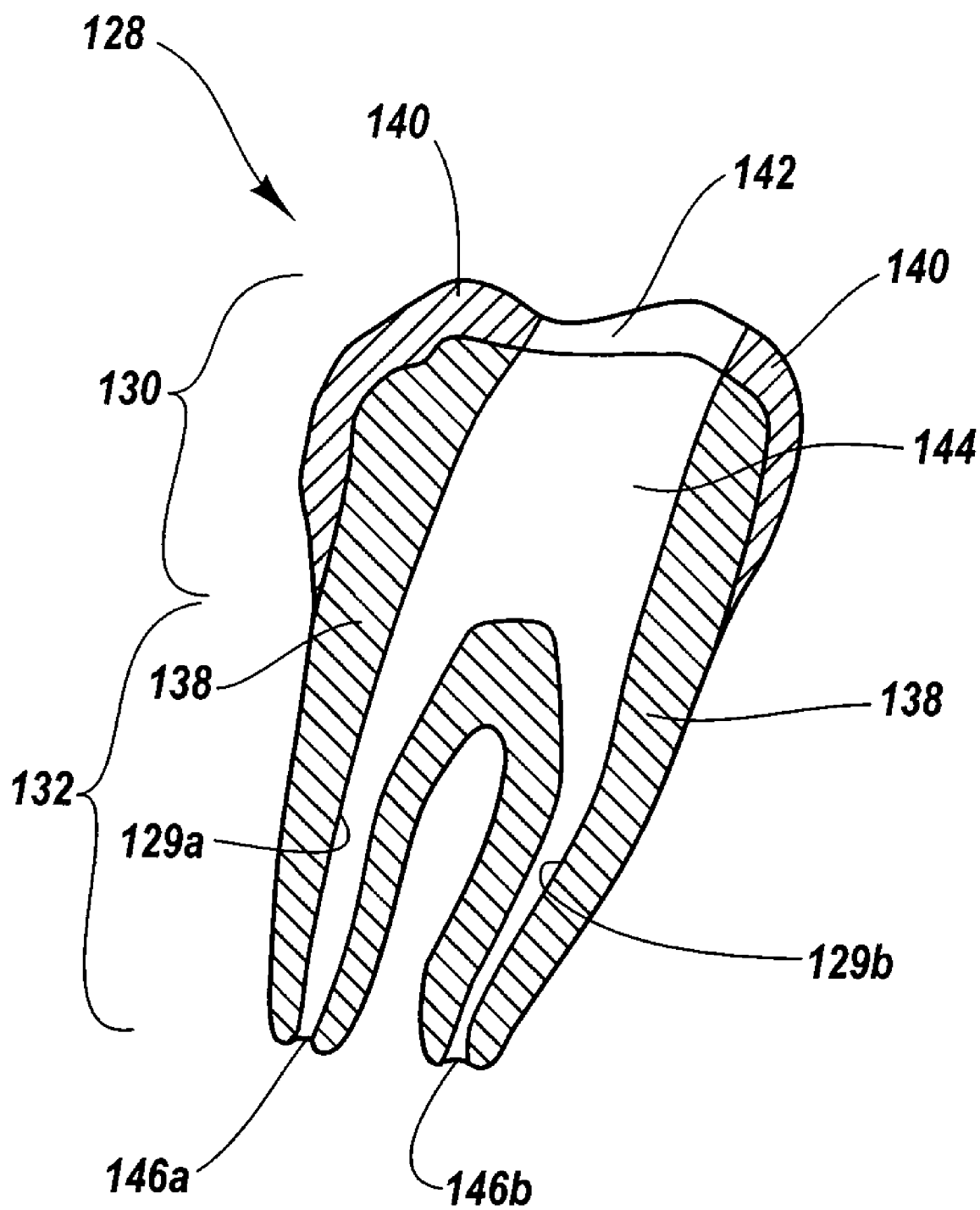
FIG. 3 illustrates an endodontically prepared root canal chamber of a diseased tooth.

FIG. 3 shows a cross-sectional view of a tooth 128 that has been endodontically prepared by removing pulp and other soft tissue material from the root canal chambers 129a and 129b. Tooth 128 includes a crown portion 130 and a root portion 132. The tooth is composed of dentin material 138 with the crown 130 being covered by enamel 140.

In FIG. 3, a portion of the enamel and dentin have been removed from the crown 130 (e.g., by drilling) to form an access opening 142 providing access to the interior of the crown. The pulp material originally present within the crown interior and root canals 129a and 129b has been removed by conventional endodontic procedures (e.g., using one or more endodontic files). Each root canal terminates at an apex 146*a* and 146*b* respectively.

In FIG. 4A the practitioner is shown inserting an endodontic cone 102 into chamber 112 so as to coat at least a portion of the outside surface of cone 102 with adhesive composition 110. Advantageously, the coating of cone 102 is accomplished with relatively little or no mess, as the practitioner is able to easily insert one or more cones 102 into chamber 112 and then withdraw each cone 102, as shown in FIG. 4B.

Figure 5:
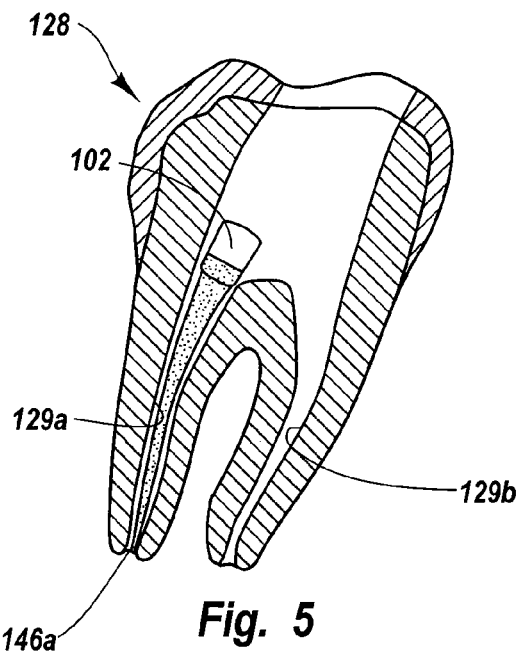
FIG. 5 illustrates a coated endodontic cone inserted within a root canal of a tooth.

Referring to FIG. 5, the adhesive endodontic cone 102 is inserted in the prepared root canal 129*a* of tooth 128 and is pushed into the canal 129*a* until fully inserted so as to reach apex 146*a*. One or more coated endodontic cones 102 may be inserted into each root canal, as required, to fill the root canal chamber. If multiple cones are used, they may be packed down into the desired position. Root canal 129*b* is filled with one or more chair-side coated endodontic cones 102 in the same way as root canal 129*a*.

Figure 6:
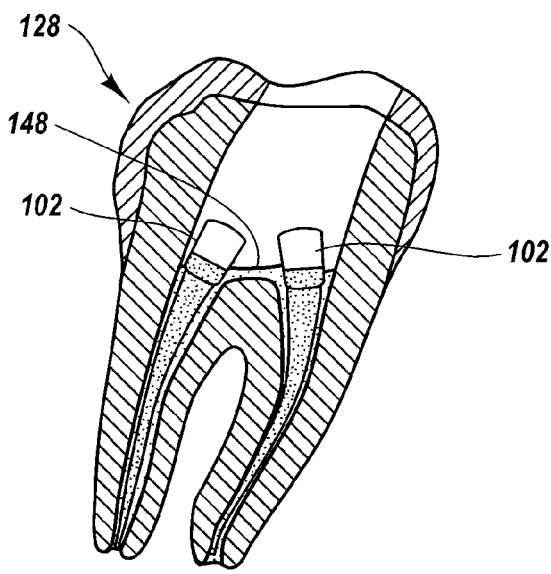
FIG. 6 illustrates an endodontic sealing composition introduced into the prepared root canal and surrounding the endodontic cone of FIG. 5.

Referring to FIG. 6, an endodontic sealing composition 148 is used to fill any spaces between the endodontic cones 102 and the sides of root canal chambers 129*a* and 129*b*. The endodontic sealing composition 148 may be introduced into the root canal chamber before, after, or simultaneously with the coated endodontic cone 102.

A hydrophilic resin, such as Endo-REZ, available from Ultradent Products, Inc., is preferred because of its ability to penetrate into the hydrophilic dentinal tubules and side canals of the chamber, facilitating a strong and complete seal between the hydrophilic tissue of the chamber and the adhesive coated endodontic cone. A variety of exemplary suitable endodontic sealing resins suitable for use with the inventive endodontic cones are disclosed in U.S. Pat. Nos. 6,500,004, 6,652,282, and U.S. patent application Ser. No. 11/109,424 filed Apr. 19, 2005. For purposes of disclosing endodontic sealing compositions, the foregoing patents and application are incorporated by reference. Because of the depth of the root canal, it is preferable that endodontic sealing composition 148 be a chemical cure resin, although a light curable resin could alternatively be used with appropriate care. Endo-REZ is a suitable two-part chemical cure sealing resin comprising a hydrophilic polymerizable resin and an initiator-amine activator curing system (e.g., P-Tide and benzoyl peroxide) that may be used to seal the area between the canal surface and the adhesive coated endodontic cone 102. A dual cure Endo-REZ may also be used, which can be light cured to reduce the time when a filling material may be placed over the filled root canal (e.g., by accelerating curing of at least the top surface of the sealing resin after placement in the root canal).

Advantageously, no separate curing step for curing adhesive composition 110 prior to insertion into the root canal is required with the inventive chair-side coating technique. Rather, curing of composition 110 may be triggered by initiators and/or amine activators present within sealing composition 148. It may be helpful to include an initiator or an amine activator within the adhesive composition 110, so as to ensure sufficient free-radical formation for polymerization. As such, all that is required of the practitioner is to dip one or more of cones 102 into the chamber 112 of micro-dose container 104, and then insert one or more cones coated with the adhesive composition into the root canal chamber to be filled, either before, during, or after introducing the sealing composition 148. Advantageously, the initiator-amine activator curing system within the sealing composition may be used to initiate polymerization of the adhesive resin compound and any additional polymerizable thinning agents within the adhesive composition at the same time as the sealing composition is cured. Although not required, it has been found advantageous to include an initiator or amine activator within the adhesive composition to ensure adequate polymerization and adhesion between the hydrophobic substrate of the endodontic cone and the adhesive composition, and between the adhesive composition and the sealing composition.

Figure 7:
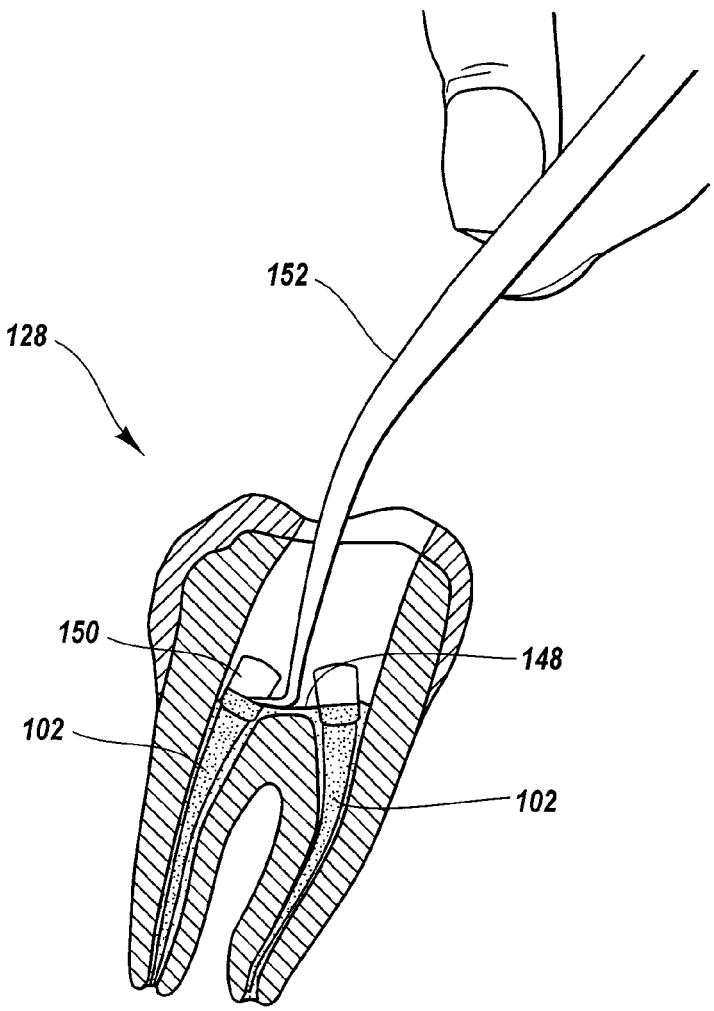
FIG. 7 illustrates removal of the hub of the coated endodontic cone.

As illustrated in FIG. 7, once sufficiently cured, the hub 150 of the adhesive endodontic cone 102 may be removed, such as by instrument 152, so as to form a uniform, smooth surface. The filled root canal chamber is now ready for further treatment, such as placement of a post, a crown, a composite resin or other procedures known in the art.

IV. Exemplary Adhesive Compositions

Example 1

An exemplary adhesive composition was formed by mixing together the following components. All percentages are by weight unless otherwise indicated:

| | |
|---|---|
| Methacrylate grafted polybutadiene | 15% |
| Urethane dimethacrylate | 59% |
| Triethylene Dimethacrylate | 25% |
| P-Tide | 1% |

Example 2

An exemplary adhesive composition was formed by mixing together the following components:

| | |
|---|---|
| Methacrylate grafted polybutadiene | 30% |
| Butyl methacrylate | 20% |
| 1,6 hexanediol dimethacrylate | 30% |
| PEGDA | 19.45% |
| Benzyl peroxide (BPO) | 0.5% |
| 2,6-di-tert buty-4-methylphenol (BHT) | 0.05% |

Example 3

An exemplary adhesive composition was formed by mixing together the following components:

| | |
|---|---|
| Methacrylate grafted polybutadiene | 20% |
| Butyl methacrylate | 20% |
| 1,6 hexanediol dimethacrylate | 59.45% |
| Benzyl peroxide (BPO) | 0.5% |
| BHT | 0.05% |

Example 4

An exemplary adhesive composition was formed by mixing together the following components:

| | |
|---|---|
| Methacrylate grafted polybutadiene | 25% |
| 1,6 hexanediol dimethacrylate | 74.45% |
| Benzyl peroxide (BPO) | 0.5% |
| BHT | 0.05% |
| Butyl methacrylate | 20% |

Example 5

An exemplary adhesive composition was formed by mixing together the following components:

| | |
|---|---|
| Methacrylate grafted polybutadiene | 25% |
| 1,6 hexanediol dimethacrylate | 74.45% |
| P-Tide | 0.5% |

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A kit for chair-side coating of an endodontic cone preparatory to sealing a root canal comprising:
    at least one elastomeric endodontic cone comprising a hydrophobic elastomer substrate and that is sized and shaped so as to be at least partially insertable into an exposed root canal of a tooth; and
    a container having a chamber containing therein a polymerizable adhesive composition;
    wherein the polymerizable adhesive composition includes an adhesive resin compound comprised of a hydrophobic region for adhering to the hydrophobic elastomer of the elastomeric endodontic cone and a hydrophilic region that is chemically compatible with a hydrophilic sealing resin, wherein the polymerizable adhesive composition further comprises one of an initiator or an amine activator, but not both, so as to prevent hardening of the polymerizable adhesive composition prior to chair-side coating of the hydrophobic elastomer substrate;
    wherein the kit facilitates chair-side coating of the at least one elastomeric endodontic cone with the polymerizable adhesive composition by a dental practitioner.

2. A kit as recited in claim 1, wherein the chamber of the container has a volume between about 20 and about 55 microliters.

3. A kit as recited in claim 1, wherein the hydrophobic elastomer substrate comprises gutta percha.

4. A kit as recited in claim 1, wherein the hydrophobic elastomer substrate comprises at least one of synthetic rubber, natural rubber, a derivative of natural rubber, silicone rubber, neoprene, isoprene, or polybutadiene.

5. A kit as recited in claim 1, wherein the polymerizable adhesive composition further comprises a thinning agent that reduces the viscosity of the polymerizable adhesive composition.

6. A kit as recited in claim 5, wherein the thinning agent comprises a polymerizable resin.

7. A kit as recited in claim 5, wherein the thinning agent comprises about 50% to about 95% by weight of the adhesive composition.

8. A kit as recited in claim 5, wherein the thinning agent comprises about 60% to about 85% by weight of the adhesive composition.

9. A kit as recited in claim 5, wherein the thinning agent comprises about 65% to about 80% by weight of the adhesive composition.

10. A kit as recited in claim 1, wherein the adhesive resin compound comprises about 5% to about 50% by weight of the adhesive composition.

11. A kit as recited in claim 1, wherein the adhesive resin compound comprises about 10% to about 40% by weight of the adhesive composition.

12. A kit as recited in claim 1, wherein the adhesive resin compound comprises about 15% to about 30% by weight of the adhesive composition.

13. A kit as recited in claim 1, wherein the adhesive resin compound comprises at least one hydrophobic backbone that is chemically compatible with the hydrophobic elastomer of the endodontic cone, at least one urethane constituent on at least one side of the backbone, and at least one methacrylate constituent adjacent to the urethane constituent.

14. A kit as recited in claim 13, wherein the backbone comprises a hydrophobic polymer chain.

15. A kit as recited in claim 14, wherein the hydrophobic polymer chain comprises at least one of polybutadiene, polyethylene glycol, polypropylene glycol, or polyhexatetramethyleneether-glycol.

16. A kit for chair-side coating of an endodontic cone preparatory to sealing a root canal comprising:
    at least one elastomeric endodontic cone comprising a hydrophobic elastomer substrate and that is sized and shaped so as to be at least partially insertable into an exposed root canal of a tooth; and
    a container having a chamber containing therein a polymerizable adhesive composition into which the elastomeric endodontic cone is adapted to be inserted, the container having a length, diameter, and volume configured to accept the elastomeric endodontic cone so as to allow the cone to be coated with the polymerizable adhesive composition so as to facilitate bonding between the hydrophobic substrate and a hydrophilic sealing resin within a root canal, wherein the polymerizable adhesive composition is comprised of:
        an adhesive resin compound which includes a hydrophobic region for adhering to the hydrophobic elastomer of the endodontic cone and a hydrophilic region that is chemically compatible with a hydrophilic sealing resin;
        one of an initiator or an amine activator, but not both, so as to prevent hardening of the polymerizable adhesive composition prior to chair-side coating of the hydrophobic elastomer substrate; and
        a thinning agent composed of a polymerizable resin that is suitable for use in the oral cavity and which lowers the viscosity of the polymerizable adhesive composition and facilitates coating of the endodontic cone with the polymerizable adhesive composition,
    wherein the kit facilitates chair-side coating of the at least one elastomeric endodontic cone with the polymerizable adhesive composition by a dental practitioner.

17. A kit as recited in claim 16, wherein the thinning agent includes at least one polymerizable resin selected from the group of acrylate resins, methacrylate resins, triethylene dimethacrylate, butyl methacrylate, butyl dimethacrylate, hexanediol dimethacrylate, polyethylene glycol dimethacrylate, and isobornyl methacrylate.

18. A kit as recited in claim 17, wherein the thinning agent comprises about 50% to about 95% by weight of the adhesive composition.

19. A kit for chair-side coating of an endodontic cone preparatory to sealing a root canal comprising:
    at least one elastomeric endodontic cone comprising a hydrophobic elastomer substrate and that is sized and shaped so as to be at least partially insertable into an exposed root canal of a tooth; and a container having a chamber containing therein a polymerizable adhesive composition into which the elastomeric endodontic cone is adapted to be inserted, the container having a length, diameter, and volume configured to accept the elastomeric endodontic cone so as to allow the cone to be coated with the polymerizable adhesive composition and facilitate bonding between the hydrophobic elastomer substrate and a hydrophilic sealing resin within a root canal, wherein the a polymerizable adhesive composition is comprised of:
- an adhesive resin compound which includes a hydrophobic region for adhering to the hydrophobic elastomer substrate of the endodontic cone and a hydrophilic region that is chemically compatible with a hydrophilic sealing resin; and
- one component of a two-component initiator-amine activator system that promotes curing of the adhesive resin upon later contacting the polymerizable adhesive composition with a complementary component of the two-component initiator-amine activator system during use,
- wherein the polymerizable adhesive composition includes only one component of a two-component initiator-amine activator system, but not both, so as to prevent hardening of the polymerizable adhesive composition prior to chair-side coating of the hydrophobic elastomer substrate,
- wherein the kit facilitates chair-side coating of the at least one elastomeric endodontic cone with the polymerizable adhesive composition by a dental practitioner.

20. A kit as recited in claim 19, wherein the polymerizable adhesive composition further comprises a thinning agent composed of a polymerizable resin that is suitable for use in the oral cavity, which lowers the viscosity of the polymerizable adhesive composition and facilitates coating of the endodontic cone with the polymerizable adhesive composition.

21. A kit as recited in claim 20, wherein the thinning agent comprises about 50% to about 95% by weight of the polymerizable adhesive composition.

22. A kit for chair-side coating of an endodontic cone preparatory to sealing a root canal comprising:
- at least one elastomeric endodontic cone comprising a hydrophobic elastomer substrate and that is sized and shaped so as to be at least partially insertable into an exposed root canal of a tooth; and
- a container having a chamber containing therein a polymerizable adhesive composition,
- wherein the polymerizable adhesive composition includes an adhesive resin compound comprised of a hydrophobic region for adhering to the hydrophobic elastomer of the elastomeric endodontic cone and a hydrophilic region that is chemically compatible with a hydrophilic sealing resin, wherein the polymerizable adhesive composition further comprises only one component of an initiator-amine activator curing system, but not both, so as to prevent hardening of the polymerizable adhesive composition prior to chair-side coating of the hydrophobic elastomer substrate; wherein the one component is an initiator;
- wherein the kit facilitates chair-side coating of the at least one elastomeric endodontic cone with the polymerizable adhesive composition by a dental practitioner.

23. A kit for chair-side coating of an endodontic cone preparatory to sealing a root canal comprising:
- at least one elastomeric endodontic cone comprising a hydrophobic elastomer substrate and that is sized and shaped so as to be at least partially insertable into an exposed root canal of a tooth; and
- a container having a chamber containing therein a polymerizable adhesive composition,
- wherein the polymerizable adhesive composition includes an adhesive resin compound comprised of a hydrophobic region for adhering to the hydrophobic elastomer of the elastomeric endodontic cone and a hydrophilic region that is chemically compatible with a hydrophilic sealing resin, wherein the polymerizable adhesive composition further comprises only one component of an initiator-amine activator curing system, but not both, so as to prevent hardening of the polymerizable adhesive composition prior to chair-side coating of the hydrophobic elastomer substrate; wherein the one component is an amine-activator;
- wherein the kit facilitates chair-side coating of the at least one elastomeric endodontic cone with the polymerizable adhesive composition by a dental practitioner.

* * * * *

UNITED STATES PATENT AND TRADEMARK OFFICE
CERTIFICATE OF CORRECTION

| | |
|---|---|
| PATENT NO. | : 7,833,015 B2 |
| APPLICATION NO. | : 11/691052 |
| DATED | : November 16, 2010 |
| INVENTOR(S) | : Tuttle et al. |

Page 1 of 1

It is certified that error appears in the above-identified patent and that said Letters Patent is hereby corrected as shown below:

<u>Column 5</u>
Line 36, after "into the" insert --root canal, simplifying the overall procedure.--

<u>Column 13</u>
Line 11 claim 19, remove [wherein the]
Line 12 claim 19, change "a" to --wherein the--

Signed and Sealed this
Twenty-sixth Day of April, 2011

David J. Kappos
*Director of the United States Patent and Trademark Office*